United States Patent [19]
Pedersen et al.

[11] Patent Number: 6,154,668
[45] Date of Patent: Nov. 28, 2000

[54] AMBULATORY RECORDER HAVING A REAL TIME AND NON-REAL TIME PROCESSORS

[75] Inventors: Henrik E. Pedersen, Vanloese, Denmark; Malcolm G. S. Williams, Stockholm; Alain Minoz, Bromma, both of Sweden; Arch W. Butler, St. Louis Park, Minn.

[73] Assignee: Medtronics Inc., Minneapolis, Minn.

[21] Appl. No.: 09/130,148

[22] Filed: Aug. 6, 1998

[51] Int. Cl.[7] ....................................................... A61B 5/05
[52] U.S. Cl. ........................... 600/361; 600/300; 600/431
[58] Field of Search ................................... 600/300–301, 600/345–347, 361–365, 509, 546, 431, 433, 435; 128/904, 903, 920–925

[56] References Cited

U.S. PATENT DOCUMENTS

| | | | |
|---|---|---|---|
| D. 396,037 | 7/1998 | Cappa et al. ...................... | D14/114.5 |
| 3,898,984 | 8/1975 | Mandel et al. ...................... | 128/2.1 A |
| 3,941,137 | 3/1976 | Vredenbregt et al. .............. | 128/423 R |
| 4,003,379 | 1/1977 | Ellinwood, Jr. ..................... | 128/260 |
| 4,082,084 | 4/1978 | Lipscher ................................. | 128/2 D |
| 4,129,125 | 12/1978 | Lester et al. ........................ | 128/2.05 R |
| 4,183,354 | 1/1980 | Sibley et al. ............................ | 128/711 |
| 4,198,963 | 4/1980 | Barkalow et al. ........................ | 128/53 |
| 4,333,475 | 6/1982 | Moreno et al. .......................... | 128/711 |

(List continued on next page.)

FOREIGN PATENT DOCUMENTS

0 356 603  9/1988  Sweden ........................... A61B 5/04

*Primary Examiner*—Cary O'Connor
*Assistant Examiner*—Michael Astorino
*Attorney, Agent, or Firm*—Thomas F. Woods; Michael J. Jaro; Harold Patton

[57] ABSTRACT

An ambulatory recorder having real time non-real time processors is described. The real time processor handles sampling functions while the non real time processor handles other functions, such as high processing operations associated with multitasking, graphical user interface, floating point calculation, Infra Red communication and long term memory storage. The second processor is primarily provided to operate a Windows CE operating system as well as one or more embedded applications. Through this design, electrical power provided by a battery is only consumed by those components essential to device operation at any particular time.

10 Claims, 5 Drawing Sheets

U.S. PATENT DOCUMENTS

| | | | |
|---|---|---|---|
| 4,353,375 | 10/1982 | Colburn et al. | 128/782 |
| 4,365,636 | 12/1982 | Barker | 128/716 |
| 4,370,983 | 2/1983 | Lichtenstein | 128/630 |
| 4,464,172 | 8/1984 | Lichtenstein | 604/65 |
| 4,503,859 | 3/1985 | Petty et al. | 128/635 |
| 4,529,401 | 7/1985 | Leslie et al. | 604/131 |
| 4,531,527 | 7/1985 | Reinhold, Jr. et al. | 128/696 |
| 4,592,018 | 5/1986 | Wiegman | 365/63 |
| 4,628,928 | 12/1986 | Lowell | 128/303 R |
| 4,632,119 | 12/1986 | Reichstein | 128/632 |
| 4,667,682 | 5/1987 | Ihlenfeld, III | 128/711 |
| 4,684,367 | 8/1987 | Schaffer et al. | 604/140 |
| 4,715,385 | 12/1987 | Cudahy et al. | 128/710 |
| 4,748,562 | 5/1988 | Miller et al. | 364/415 |
| 4,771,772 | 9/1988 | DeWitt | 128/303 R |
| 4,774,956 | 10/1988 | Kruse et al. | 128/635 |
| 4,794,934 | 1/1989 | Motoyama et al. | 128/734 |
| 4,895,161 | 1/1990 | Cudahy et al. | 128/710 |
| 4,900,305 | 2/1990 | Smith et al. | 604/65 |
| 4,917,092 | 4/1990 | Todd et al. | 128/421 |
| 4,974,599 | 12/1990 | Suzuki | 128/696 |
| 5,002,062 | 3/1991 | Suzuki | 128/696 |
| 5,007,427 | 4/1991 | Suzuki et al. | 128/659 |
| 5,010,888 | 4/1991 | Jadvar et al. | 128/696 |
| 5,012,411 | 4/1991 | Policastro et al. | 364/413.06 |
| 5,016,636 | 5/1991 | Kulakowski | 128/644 |
| 5,042,481 | 8/1991 | Suziki et al. | 128/639 |
| 5,072,458 | 12/1991 | Suzuki | 2/102 |
| 5,086,778 | 2/1992 | Mueller et al. | 128/696 |
| 5,107,835 | 4/1992 | Thomas | 128/419 R |
| 5,111,396 | 5/1992 | Mills et al. | 364/413.06 |
| 5,111,818 | 5/1992 | Suzuki et al. | 128/644 |
| 5,113,869 | 5/1992 | Nappholz | 128/696 |
| 5,117,827 | 6/1992 | Stuebe et al. | 128/635 |
| 5,131,816 | 7/1992 | Brown et al. | 417/2 |
| 5,158,083 | 10/1992 | Sacristan et al. | 128/635 |
| 5,188,104 | 2/1993 | Wernicke et al. | 128/419 R |
| 5,213,568 | 5/1993 | Lattin et al. | 604/20 |
| 5,222,503 | 6/1993 | Ives et al. | 128/731 |
| 5,224,485 | 7/1993 | Powers et al. | 128/696 |
| 5,226,431 | 7/1993 | Bible et al. | 128/904 |
| 5,228,450 | 7/1993 | Sellers | 128/711 |
| 5,238,001 | 8/1993 | Gallant et al. | 128/700 |
| 5,261,401 | 11/1993 | Baker et al. | 607/9 |
| 5,263,491 | 11/1993 | Thornton | 128/774 |
| 5,273,033 | 12/1993 | Hoffman | 607/46 |
| 5,292,344 | 3/1994 | Douglas | 607/40 |
| 5,305,202 | 4/1994 | Gallant et al. | 364/413.06 |
| 5,305,761 | 4/1994 | Byrne et al. | 128/697 |
| 5,307,263 | 4/1994 | Brown | 364/413.09 |
| 5,309,920 | 5/1994 | Gallant et al. | 128/710 |
| 5,338,157 | 8/1994 | Blomquist | 417/2 |
| 5,341,291 | 8/1994 | Roizen et al. | 364/413.02 |
| 5,343,870 | 9/1994 | Gallant et al. | 128/711 |
| 5,355,892 | 10/1994 | Saltzstein | 128/710 |
| 5,368,562 | 11/1994 | Blomquist et al. | 604/65 |
| 5,381,351 | 1/1995 | Kwong et al. | 364/571.04 |
| 5,388,587 | 2/1995 | Knutsson et al. | 128/741 |
| 5,411,022 | 5/1995 | McCue et al. | 128/632 |
| 5,429,602 | 7/1995 | Hauser | 604/65 |
| 5,431,634 | 7/1995 | Brown | 604/513 |
| 5,432,698 | 7/1995 | Fujita | 364/413.02 |
| 5,438,985 | 8/1995 | Essen-Moller | 128/633 |
| 5,479,019 | 12/1995 | Gross | 250/345 |
| 5,479,935 | 1/1996 | Essen-Moller | 128/734 |
| 5,507,904 | 4/1996 | Fisher et al. | 156/252 |
| 5,526,809 | 6/1996 | Fiddian-Green | 128/632 |
| 5,545,183 | 8/1996 | Altman | 607/5 |
| 5,607,460 | 3/1997 | Kroll | 607/30 |
| 5,645,068 | 7/1997 | Mezack et al. | 128/670 |
| 5,657,759 | 8/1997 | Essen-Moller | 600/300 |
| 5,701,894 | 12/1997 | Cherry et al. | 600/300 |
| 5,704,368 | 1/1998 | Asano et al. | 128/733 |
| 5,704,890 | 1/1998 | Bliss et al. | 600/1 |
| 5,749,907 | 5/1998 | Mann | 607/27 |

AMBULATORY RECORDER HAVING A REAL TIME AND NON-REAL TIME PROCESSORS

FIELD OF THE INVENTION

The present invention relates to ambulatory recording, for medical and especially for diagnostic purposes, and particularly to an ambulatory recorder having a real time processor and a non-real time processor.

BACKGROUND OF THE INVENTION

Various physiologic signals are often recorded and analyzed. These signals may include digestive pH signals, various digestive motility signals, pressure signals, EEG signals and EMG signals, to list only a few.

Typically, physicians require the concurrent recording of a variety of physiologic signals. For example, gastric pH signals are often collected at the same time as pressure signals. Through the concurrent collection of various parameters the physician may better understand the patient's condition.

Ambulatory recording and recorders are widely used to collect such data. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG data (Electrocardiogram), EEG data (Electroencephalogram), and pH or pressure data (Motility) in the gastrointestinal tract. Preferably such a recorder should be able to record among a programmable number of channels at a variety of programmable frequencies.

Among the problems associated with current recorders, however, is energy usage. Such recorders, because they must be ambulatory, are battery powered. Thus an ambulatory medical recorder must minimize energy usage while performing almost constant sampling across a variable number of channels at one or more frequencies.

SUMMARY OF THE INVENTION

An ambulatory recorder having a real time processor and a non-real time processor is described. The real time processor handles sampling functions while the non-real time processor handles other functions, such as high speed processing operations associated with multitasking, graphical user interface, floating point calculation, Infra Red communication and long term memory storage. In particular, the second processor is primarily provided to operate a Windows CE operating system as well as one or more embedded applications. Through this design power is only consumed by those components essential to the device operation. That is, only the real time or sampling processor operates while sampling is occurring. The non-real time or operating system processor operates only as needed, such as when logging sampled data into long term memory, re-configuring system settings (e.g., sampling frequency or channels to be sampled). In this manner an ambulatory medical recorder may be fashioned which has minimal power consumption while still offering many features.

BRIEF DESCRIPTION OF THE DRAWINGS

The Figures are not necessarily to scale.

DETAILED DESCRIPTION OF THE DRAWINGS

Figure 1A:
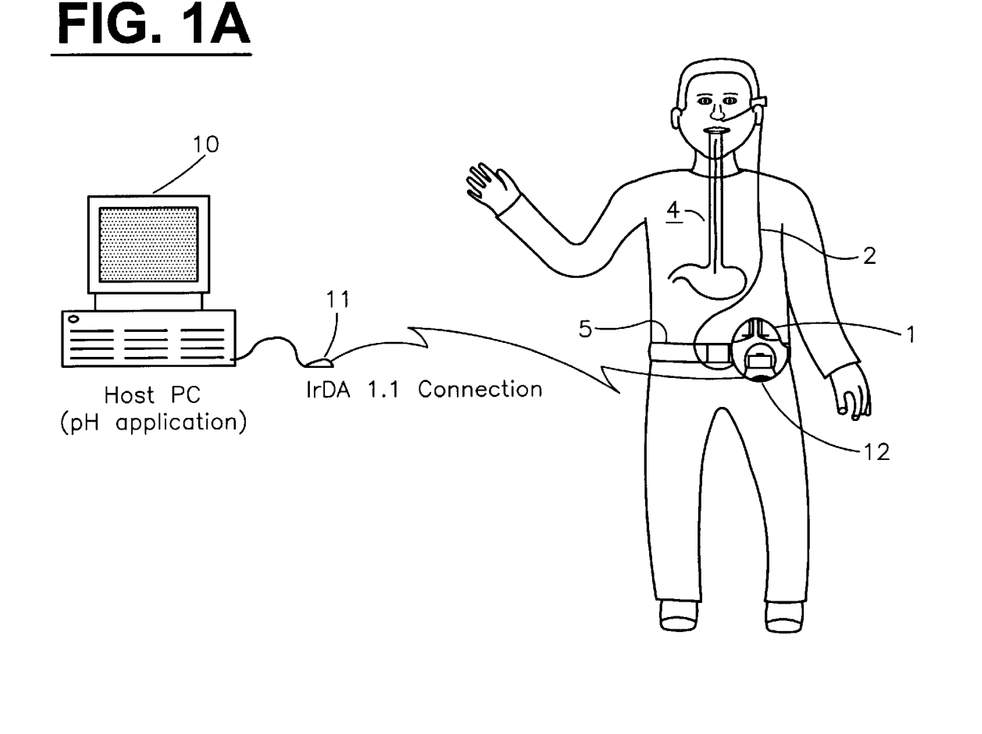
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, recorder 1 may be either carried through a mounting in the back of the recorder enclosure which fastens to patient's belt 5, or the same mounting may be coupled to be carried using a shoulder harness (not shown). Recorder 1 is coupled to patient 4 through one or more sensing catheters 2. Sensing catheters may be positioned in any area of the patient's body from which data is to be sensed, including the esophagus, as depicted in this FIG. 1A. It should be noted that the ambulatory recorder of the present invention may be used to collect many or various types of data including gastrointestinal (including pH and pressure) data, neurological data, as well as neuromuscular data, EEG data or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G91-7. While a single catheter 2 is shown depicted in this figure, recorder 1 further permits two separate sensors to be coupled to the device, as seen in FIG. 1B.

As further seen in this figure, the recorder may also communicate with a host PC 10 via an infra red data link facility through an IrDA connection 11 such as, for example, a JETEYE ESI-57680 available form Extended Systems, Inc., Boise, Id., which communicates with the recorder using the infra Red Data Association 1.1 Connection Protocol. As seen, infra red data connection makes a link to infra red port 12 on recorder 1.

Figure 1B:
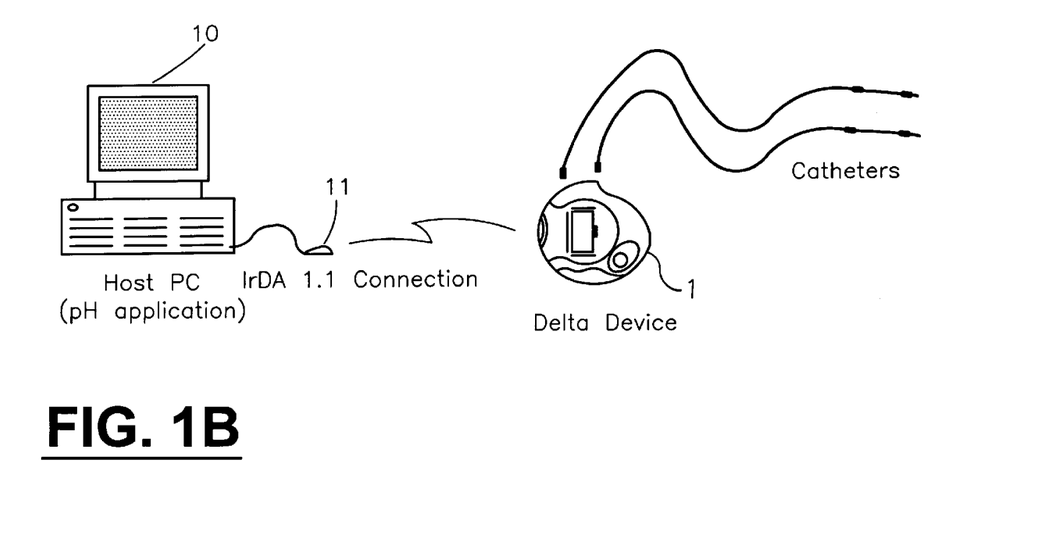
FIG. 1B illustrates a further manner in which recorder 1 may also have an infra red data communication link established with a host PC.

FIG. 1B illustrates a further manner in which recorder 1 may also have an infra red data communication link established with a host PC. In particular, infra red data communication may be further established when the recorder is not worn by the patient. As discussed in more detail below, one of the advantages of the present invention is that the infra red data components and recorder case permit such a link to be made when the device is worn as shown in FIG. 1A, as well as when the device is removed from the patient and positioned in proximity to mouse 11.

Figure 2:
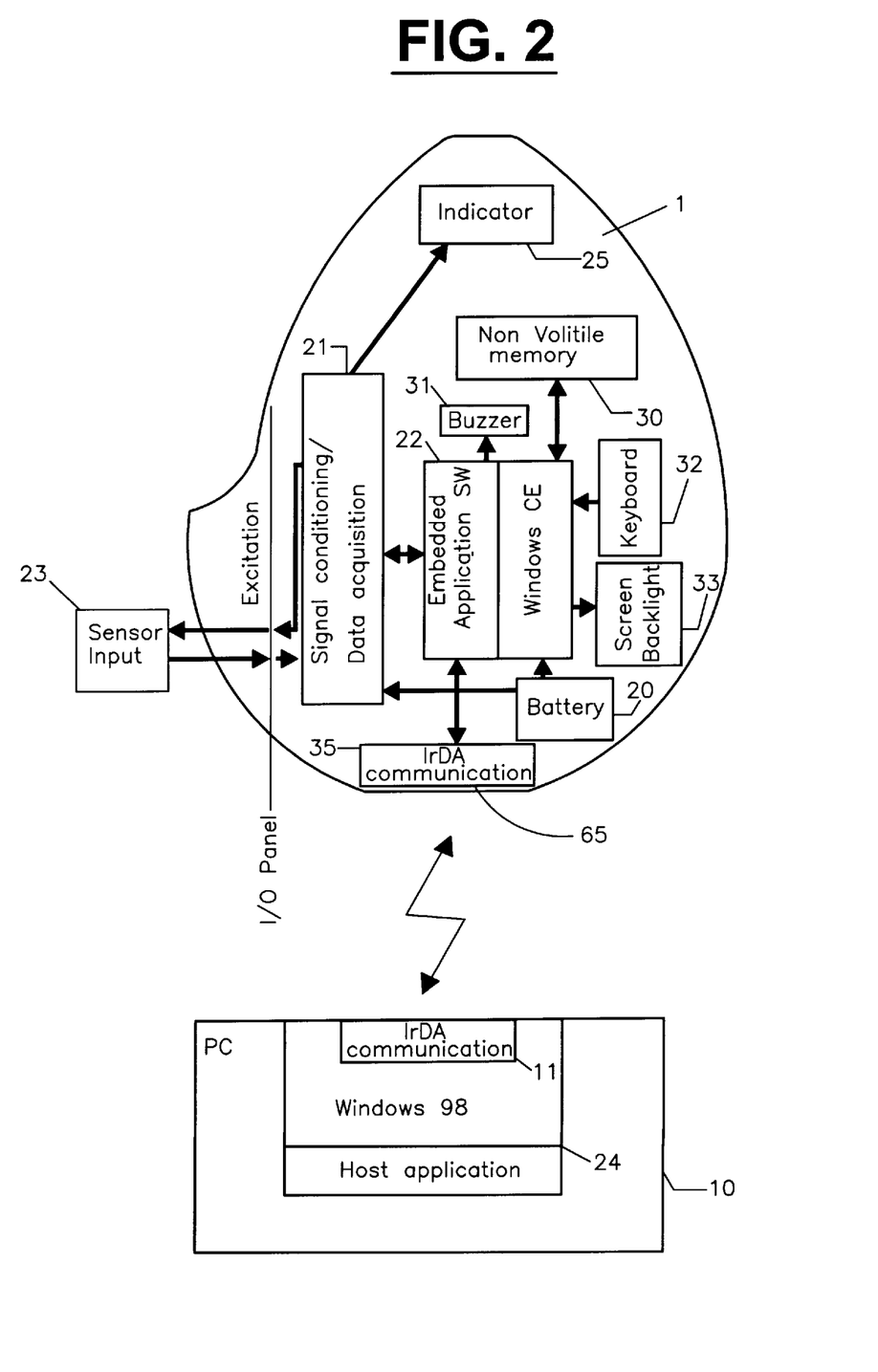
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by real time processor 21, the battery being coupled as well as to non-real time processor 22 that runs the application. As disclosed in more detail below, first real time processor 21 is a low power processor which is used to sample data received from sensor input 23 having a sensor attached thereto (not shown in FIG. 2).

Sampling is achieved through the signal conditioning block providing an excitation to the sensor coupled to sensor input 23. Such excitation voltage is often used to power and thus permit sensing to occur in a variety of different types of sensors, including pressure sensors, as is well known in the art. The sampling and sensing controls are provided by real time processor 21. Real time processor 21 also drives LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, the second processor is primarily provided to operate a Windows CE operating system, as well as one or more embedded applications, as depicted. As further seen, processor 22 is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder 1 features an infra red port 35 to communicate with the host PC. As depicted in FIG. 1B, the infra red connection permits recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In a preferred embodiment of the present invention real time processor 21 is a model PIC16LC67 IC from Microchip Technology Inc., Chandler, Ariz.; non-real time processor 22 is a model ElanSC400 IC from Advanced Micro Devices, Inc. Sunnyvale, Calif.; and non-volatile memory 30 a model Minicard AMMCL004AWP from Advanced Micro Devices, Inc. Sunnyvale, Calif.

Figure 3:
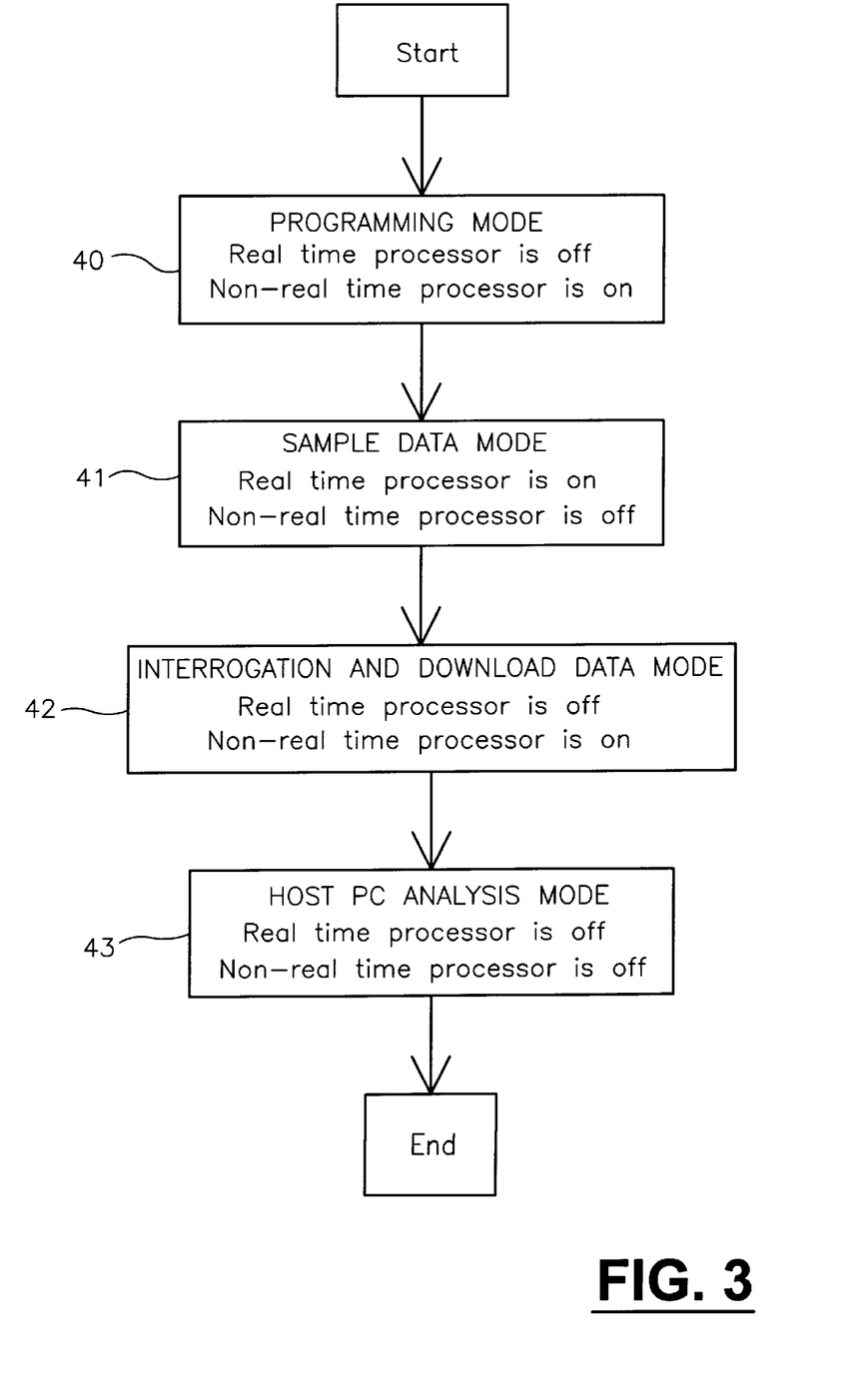
FIG. 3 depicts the basic operational steps of the present invention.

FIG. 3 depicts the basic operational steps of the present invention In particular, this FIG. depicts the advantage and utility of the dual processor architecture which is used in data recorder 1. That is, data recorder 1 is able to have only a particular and specialized processor powered during those times at which that type of processor operation is required.

As depicted, the system operational steps comprise essentially four time periods. In the first time period device programming 40 is performed. During this phase the host PC has an infra red data connection provided to recorder 1 and non-real time processor 22 has power provided thereto by battery 20. Through this connection the application is loaded into recorder 1 such that the type of catheter coupled to the device may be provided to the recorder, the number of and frequency upon which data is to be recorded is provided, the type of excitation voltages and patterns necessary for such catheters is also provided.

As further seen, during the step of programming, real time processor 21 is turned off and the device is not collecting data. Next, the system enters into a recording data mode, and during this mode non-real time processor 22 is powered down (i.e., turned off) and only real time processor 21 is activated. In particular, and as more thoroughly disclosed below, this real time processor is only provided powered on and awake at defined predetermined time periods during which data is to be collected. Thus, during those times in which no sampling is to occur, processor 21 is only power upon request or as needed. In regular intervals and for very short periods of time, non-real time processor 22 is awakened to collect blocks of data and to save same to non-volatile memory 30. The interposed sleep modes permit the device to draw a minimal amount of current from battery 20 and thus permit the recorder to acquire more data than would otherwise be possible.

Next, after the desired amount of data sampling has occurred, the device enters into an interrogation and download data mode 42. This mode is entered into by again making infra red connection with the host PC, as described above. At this time the real time processor 21 is powered down, the non-real time processor 22 is powered up, and the memory contents are transferred from the recorder to the host PC. Finally, the system enters into a host PC analysis mode 43. In this mode, data downloaded from the recorder are analyzed and/or manipulated by host PC in any suitable manner to permit the physician to extract that information which is desired.

Figure 4:
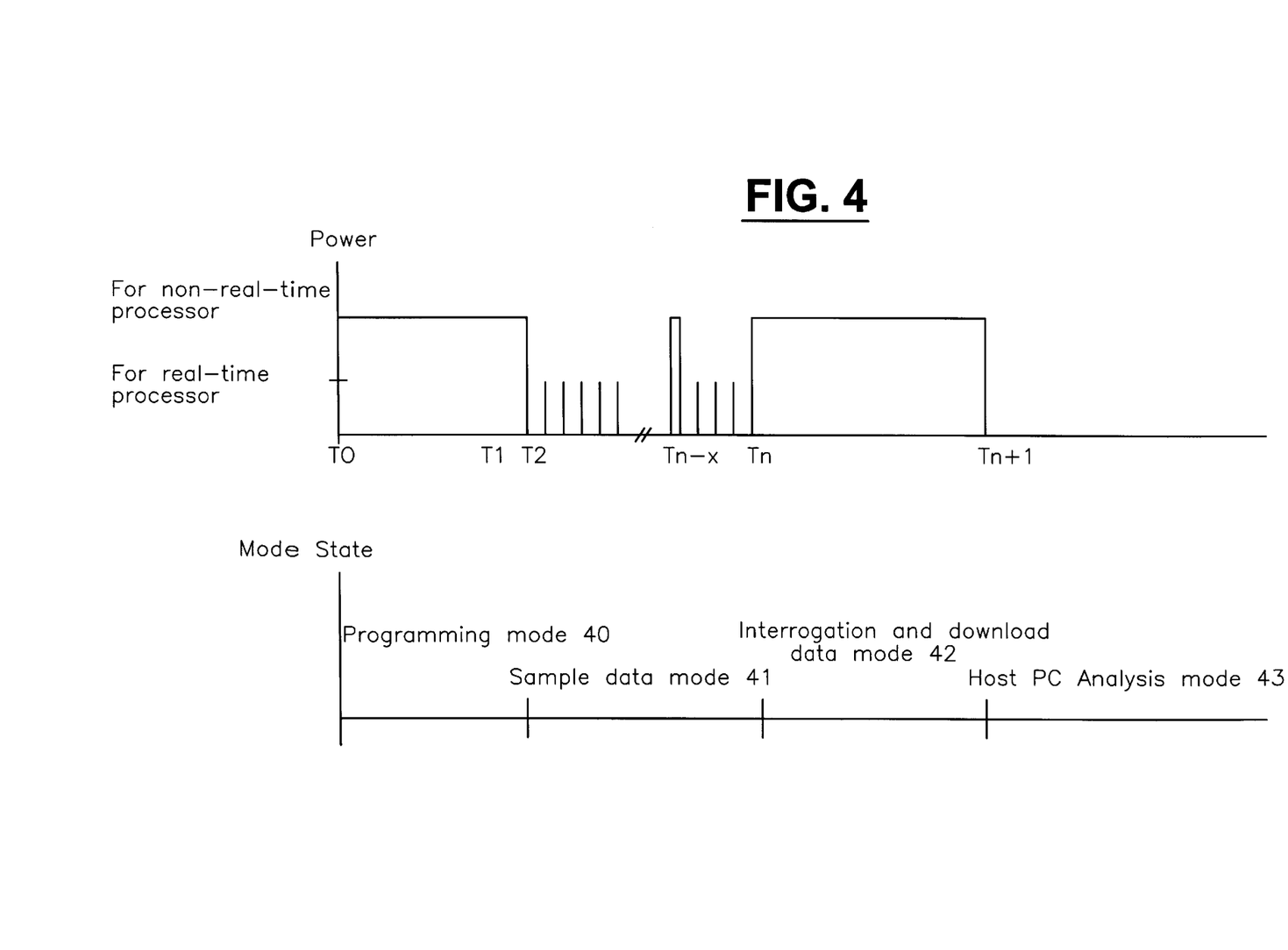
FIG. 4 illustrates, over time, the relative periods during which real time processor 21 and non-real time processor 22 are awake or in operation.

FIG. 4 illustrates, over time, the relative periods during which the real time processor 21 and non-real time processor 22 are awake or in operation. As seen, from time $T_0$ to time $T_1$, the non-real time processor 22 is in operation and, effectively, the device is in the programmer mode 40, described above. At this time, due to the current required to operate this processor, the overall power consumed by the non-real time processor 22 is $P_{non-real}$. Next, the device enters the sample data mode 41 during which time the non-real time processor 22 is turned off and the real time processor 21 is turned on. As seen, this is depicted as individual power spikes at times $T_2$–$Tn$. Moreover, the magnitudes of the individual power spikes corresponding with the awakening of the real time processor 21 are of lower magnitude than those corresponding to non-real time processor 22 (i.e. $P_{real}$ is less than $P_{non-real}$). As further seen, during sample data mode 41 the recorder periodically awakens non-real time processor 22, typically to transfer data captured in the volatile memory of real time processor 21 to non-volatile memory 30 of the recorder. Such an event is depicted here at $T_{n-x}$. Once sampling is completed the device enters into an interrogation and download mode 42 during which time the non-real time processor 22 is again awakened and again the corresponding current drain escalated.

Finally, the system may enter into the host PC analysis mode 43 during which time the recorder itself may be completely turned off and no power is consumed, as seen above.

Figure 5:
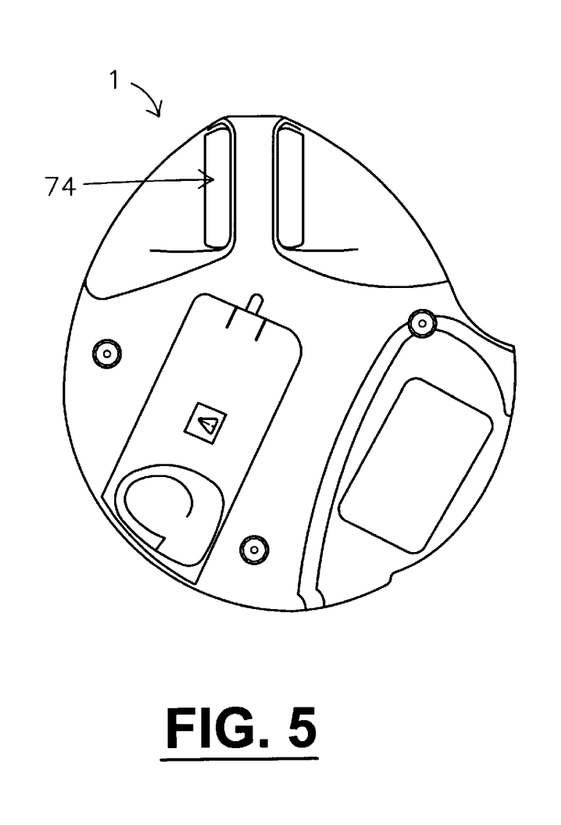
FIG. 5 is a back view of the recorder.

FIG. 5 is a back view of the recorder. As seen, recorder 1 features a belt loop 74 which may be used to mount the recorder to a patient using either the patient's belt or the shoulder strap.

Figure 6:
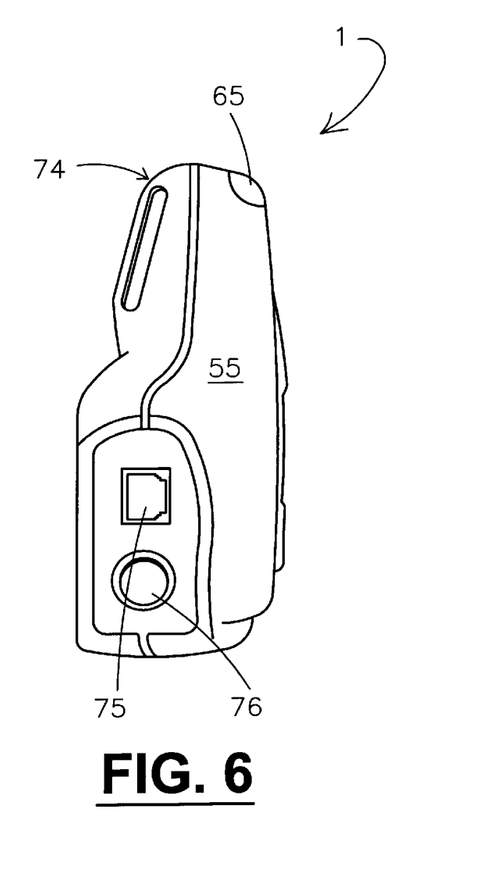
FIG. 6 is a side view of the recorder.

FIG. 6 is a side view of recorder 1. As further seen in this view, housing 55 features a pair of sensor inputs 75 and 76. In the preferred embodiment, input 75 is for a pH catheter while input 76 is for a pressure measuring catheter Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory medical data recorder for recording at least one physiological signal sensed in a patient by a sensor, the recorder comprising:

a sensor input for receiving the at least one sensed physiological signal;

at least one battery for providing a source of electrical current;

a first real time processor for controlling acquisition of the at least one sensed physiological signal during first data acquisition phases of predetermined first durations and first frequencies, the first processor being operably connected to the sensor input and powered by the at least one battery, the first processor being configured to receive, during a first awake mode, the at least one physiological signal from the sensor input and perform at least a first process thereon to yield a first data set and store same in a first memory during the data acquisition phases, and a second non-real time processor operably connected to the first data processor and powered by the at least one battery, the second processor being configured to receive, in a second awake mode, the first data set from the first processor during second data processing and storage phases of predetermined second durations and second frequencies and perform at least a second process thereon to yield a second data set and store same in a second memory during the second data processing and storage phases;

wherein the first processor is configured to enter a first sleep mode for reducing battery power consumption after the first data set has been transferred to the second processor and the second processor is operating in the second awake mode, and further wherein the second processor is configured to enter a second sleep mode for reducing battery power consumption when the first sleep mode ends and the first Processor is operating in the first awake mode.

2. The ambulatory medical data recorder of claim 1, wherein the first and second processors are operable configured such that the first data acquisition phases are of longer duration than the second data processing and storage phases.

3. The ambulatory medical data recorder of claim 1, wherein the first memory is a non-volatile memory.

4. The ambulatory medical data recorder of claim 1, wherein the second processor has means for processing the data so that processed data may be graphically displayed to a user of the recorder.

5. The ambulatory medical data recorder of claim 1, wherein the second memory is a non-volatile memory.

6. The ambulatory medical data recorder of claim 1, further comprising means for mounting the recorder to a patient.

7. The ambulatory medical data recorder of claim 1, further comprising the sensor.

8. The ambulatory medical data recorder of claim 1, wherein the sensor is a pH sensing catheter.

9. The ambulatory medical data recorder of claim 1, wherein the first processor is configured to draw less electrical current from the at least one battery than is the second processor.

10. The ambulatory medical data recorder of claim 1, further comprising means for programming the first processor to acquire a programmed number of physiological signals from the patient.

* * * * *

UNITED STATES PATENT AND TRADEMARK OFFICE
CERTIFICATE OF CORRECTION

PATENT NO.   : 6,154,668
DATED        : November 28, 2000
INVENTOR(S)  : Pedersen et al.

Page 1 of 1

It is certified that error appears in the above-identified patent and that said Letters Patent is hereby corrected as shown below:

Column 6,
Line 23, change "for mounting recorder" to -- for mounting the recorder --.

Signed and Sealed this

Eleventh Day of March, 2003

JAMES E. ROGAN
*Director of the United States Patent and Trademark Office*